US010022097B2

(12) United States Patent
Leahy et al.

(10) Patent No.: US 10,022,097 B2
(45) Date of Patent: Jul. 17, 2018

(54) DIRECT PATLAK ESTIMATION FROM LIST-MODE PET DATA

(71) Applicants: Richard M. Leahy, El Segundo, CA (US); Wentao Zhu, Houston, TX (US); Quanzheng Li, Belmont, MA (US); Bing Bai, Tustin, CA (US); Peter Stephen Conti, Pasadena, CA (US)

(72) Inventors: Richard M. Leahy, El Segundo, CA (US); Wentao Zhu, Houston, TX (US); Quanzheng Li, Belmont, MA (US); Bing Bai, Tustin, CA (US); Peter Stephen Conti, Pasadena, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 366 days.

(21) Appl. No.: 14/739,929

(22) Filed: Jun. 15, 2015

(65) Prior Publication Data
US 2015/0363948 A1    Dec. 17, 2015

Related U.S. Application Data

(60) Provisional application No. 62/012,908, filed on Jun. 16, 2014.

(51) Int. Cl.
*A61B 5/05* (2006.01)
*A61B 6/00* (2006.01)
(Continued)

(52) U.S. Cl.
CPC ............ *A61B 6/5205* (2013.01); *A61B 6/037* (2013.01); *A61B 6/0457* (2013.01);
(Continued)

(58) Field of Classification Search
CPC ............................. A61B 5/06; A61B 19/5244
See application file for complete search history.

(56) References Cited

U.S. PATENT DOCUMENTS 6,915,004 B2    7/2005    Newport et al.

OTHER PUBLICATIONS

Carson, R.E. 2003. Tracer kinetic modeling in PET. In Valk, PE, et al., eds., Positron Emission Tomography, Basic Science and Clinical Practice, Springer Vertag London Ltd. pp. 127-159.
(Continued)

*Primary Examiner* — Hien Nguyen
(74) *Attorney, Agent, or Firm* — McDermott Will Emery LLP

(57) ABSTRACT

A medical imaging system for reconstructing quantitative dynamic nuclear medicine images of a subject may include a three dimensional positron emission tomography (3D PET) scanner and a data processing system. The three dimensional positron emission tomography (3D PET) scanner may: perform scans of the subject at each of multiple bed positions, each scan being of only a sub-portion of the subject that is within an axial length covered by the scanner; and generate dynamic list-mode PET data that: represents a total number of photon pairs arriving at each of multiple detector pairs in the 3D PET scanner; and is organized in a list of elements, each element in the list including a detector pair index and an arrival time for each detected photon pair; and acquires PET data using a dynamic PET protocol with at least two scans at each of the multiple bed positions. The data processing system may: reconstruct Patlak slope and intercept images of the subject over an axial length of the subject that exceeds the axial length of each scan of the subject by optimizing a likelihood or penalized likelihood function using the list-mode PET data from at least two scans of the subject at each of the multiple bed positions; and
(Continued)

store the reconstructed image in a storage device or displays the reconstructed image on a display system.

18 Claims, 3 Drawing Sheets

(51) Int. Cl.
  *A61B 6/03* (2006.01)
  *A61B 6/04* (2006.01)
  *G06T 11/00* (2006.01)
(52) U.S. Cl.
  CPC .......... *A61B 6/4258* (2013.01); *A61B 6/4275* (2013.01); *A61B 6/504* (2013.01); *A61B 6/507* (2013.01); *G06T 11/006* (2013.01); *G06T 2207/10104* (2013.01); *G06T 2211/412* (2013.01); *G06T 2211/424* (2013.01)

(56) References Cited

OTHER PUBLICATIONS

Kamasak, M.E. et al. 2005. Direct reconstruction of kinetic parameter images from dynamic PET data. IEEE Transactions on Medical Imaging, May 2005, vol. 24, No. 5, pp. 636-650.
Karakatsanis, N.A. et al. 2013. Dynamic whole-body PET parametric imaging: I. Concept, acquisition protocol optimization and clinical application. Physics in Medicine and Biology, vol. 58, No. 29, pp. 7391-7418.
Li, Q. et al. 2006. Statistical modeling and reconstruction of randoms pre-corrected PET data, IEEE Transactions on Medical Imaging, Dec. 2006, vol. 25, No. 12, pp. 1565-1572.
Li, Q. et al. 2007. A Fast Fully 4D Incremental Gradient Reconstruction Algorithm for List Mode PET Data. IEEE Transactions on Medical Imaging, Jan. 2007, vol. 26, No. 1, pp. 58-67.
Logan, J. et al. 1990. Graphical Analysis of Reversible Radioligand Binding from Time-Activity Measurements Applied to [N-11C-methyl]-(−)-Cocaine PET studies in Human Subjects. Journal of Cerebral Blood Flow and Metabolism, vol. 10, No. 5, pp. 740-747.
Maintz, J.B.A. et al. 1998. A Survey of Medical Image Registration, Medical Image Analysis, vol. 2, No. 1, pp. 1-36.
Patlak, C.S. et al. 1983. Graphical Evaluation of Blood-to-Brain Transfer Constants from Multiple-Time Uptake Data. Journal of Cerebral Blood Flow and Metabolism, vol. 3, No. 1, pp. 1-7.
Qi, J. et al. 1998. High Resolution 3D Bayesian Image Reconstruction Using the MicroPET Small-animal Scanner. Physics in Medicine and Biology, vol. 43, No. 4, pp. 1001-1013.
Snyder, D.L. 1984. Parameter Estimation for Dynamic Studies in Emission-Tomography Systems Having List-Mode Data. IEEE Transactions on Nuclear Science, Apr. 1984, vol. NS-31, No. 2, pp. 925-931.
Wang, G. et al. 2008. Maximum a posteriori Reconstruction of Patlak Parametric Image from Sinograms in Dynamic PET. Physics in Medicine and Biology, vol. 53, pp. 593-604.
Wang, G. et al. 2009. Generalized Algorithms for Direct Reconstruction of Parametric Images From Dynamic PET Data. IEEE Transactions on Medical Imaging, Nov. 2009, vol. 28, No. 11, pp. 1717-1726.
Zhu, W. et al. 2013. Data Correction Methods for Wholebody Patlak Imaging from List-mode PET Data. 12th International Meeting on Fully Three-Dimensional Image Reconstruction in Radiology and Nuclear Medicine, Proceedings, Lake Tahoe, California, pp. 213-216.
Zhu, W. et al. 2014. Patlak Image Estimation From Dual Time-Point List-Mode PET Data. IEEE Transactions on Medical Imaging, Apr. 2014, vol. 33, No. 4, pp. 913-924.
Zhuang, H. et al. 2001. Dual Time Point 18F-FDG PET Imaging for Differentiating Malignant from Inflammatory Processes. The Journal of Nuclear Medicine, Sep. 2001, vol. 42, No. 9, pp. 1412-1417.
Picard et al., Motion Correction of PET Images Using Multiple Acquisition Frames, pp. 137-144, 1997, IEEE Transactions on Medical Imaging.†
Qi et al., A Theoretical Study of the Contrast Recovery and Variance of MAP Reconstructions from PET Data, pp. 293-305, 1999, IEEE Transactions on Medical Imaging.†
Li et al., A Fast Fully 4-D Incremental Gradient Reconstruction Algorithm for List Mode PET Data, pp. 58-67, 2007, IEEE Transactions on Medical Imaging.†
Nichols et al., Continuous Time Dynamic PET Imaging Using List Mode Data, pp. 98-111, 1999, Signal & Image Processing Institute, IPMI 99, LNCS 1613, University of Southern California, Los Angeles, CA.†
Karakatsanis et al., Dynamic whole-body PET parametric imaging: I. Concept, acquisition protocol optimization and clinical application, pp. 7391-7418, 2013, Institute of Physics and Engineering in Medicine, Phys. Med. Bio.†
Karakatsanis et al., Whole-body PET parametric imaging employing direct 4D nested reconstruction and a generalized non-linear Patlak model, 10 pages, 2014, Proceedings of SPIE, a Dpt of Radiology, School of Medicine, Johns Hopkins University, Baltimore, MD.†
Hoh et al., Whole body Patlak Imaging, 3 pages, 2003, J. Nucl. Med., UCSD Medical Center, San Diego, CA.†
Li et al., Direct Estimation of Patlak Parameters From List Mode PET Data, 390-393, 2009, IEEE Univ. of Southern California, Los Angeles, CA.†

† cited by third party

US 10,022,097 B2

DIRECT PATLAK ESTIMATION FROM LIST-MODE PET DATA

CROSS-REFERENCE TO RELATED APPLICATION

This application is based upon and claims priority to U.S. Provisional Patent Application No. 62/012,908 entitled "PATLAK IMAGE ESTIMATION FROM DUAL TIME-POINT LIST-MODE POSITRON EMISSION TOMOGRAPHY (PET) DATA" filed on Jun. 16, 2014. The entire content of this application is incorporated herein by reference.

STATEMENT REGARDING FEDERALLY SPONSORED RESEARCH

This invention was made with government support under Grants R01 EB013293 and R01 EB010197 awarded by the National Institutes of Health. The government has certain rights in the invention.

BACKGROUND

Technical Field

This disclosure relates to medical imaging, including dynamic imaging using positron emission tomography (PET) scanners that produce and process list-mode PET data collected in a dynamic protocol.

Description of Related Art

PET scanners may be used for both biomedical and neuro-scientific research and clinical studies for diagnosing and staging disease and for assessing response to therapy using radiotracers labelled with positron emitting isotopes.

The radioactive tracer may be injected before or at the start of the PET scan. One of the most commonly used radiotracers is 18F-FDG (2-deoxy-2-(18F) fluoro-D-glucose), which is a glucose analog. FDG may be used as an example, but PET can be applied with any tracer labelled with a positron emitting isotope.

Positrons may be produced from the nucleus of the radioisotopes. The annihilation of the positron with an electron after it travels a short range may produce a pair of high energy (511 keV) photons. This pair of photons may travel in approximately opposite directions, and may be detected by detectors that surround the patient (FIG. 1).

A photon pair arriving at two different detectors within a short time window may be called a coincidence or an event and may be assumed to come from the same annihilation. The difference in arrival time may also be recorded for PET scanners operating in time-of-flight model. The annihilation may be assumed to happen along the line connecting the two detectors, commonly referred to as the "line of response" (LOR). FIG. 1 illustrates examples of these as lines of response 101 and 103. List-mode data from the scanner may include a record of the LOR for each detected event and the time at which the event occurred. The PET image may be reconstructed directly from this list-mode data or the list-mode data may first be sorted into sinograms from which the PET image is reconstructed.

Traditional or static PET images may represent accumulated tracer uptake computed from PET data acquired over a single contiguous time interval, typically starting about one hour after the tracer is administered. To form static PET images that cover an axial length 201 (FIG. 2) of the patient that is longer than the axial extent 202 (FIG. 2) of the scanner, the patient lies on a bed 203 that is moved through the scanner as part of the data acquisition protocol so that time-contiguous data are acquired from each part of the patient to be imaged. The protocol may use a step and shoot mode in which the bed 203 remains stationary in each position while data is acquired. Alternatively, the bed 203 may undergo continuous rectilinear motion during data acquisition. See U.S. Pat. No. 6,915,004 B2, Newport D F, Casey M E, Luk W K, Reed J H (2002).

Static PET images may not make use of the information contained in the dynamic changes in tracer uptake which can be useful in diagnosing, staging disease, and assessing response to therapy. Changes in uptake may be assessed by comparing two images of the patient acquired over two different time intervals. See H. Zhuang, M. Pourdehnad, E. S. Lambright, A. J. Yamamoto, M. Lanuti, P. Li, P. D. Mozley, M. D. Rossman, S. M. Albelda, and A. Alavi (2001), "Dual Time Point 18F-FDG PET Imaging for Differentiating Malignant from Inflammatory Processes." J Nucl Med, 42(9): p. 1412-1417. This approach may use a two-pass scan over an axial extent that can exceed that of the scanner. The images may be reconstructed independently from the data from each pass and then compared.

In order to fit an explicit kinetic model, kinetic PET data may be continuously collected from the time the tracer is administered and then fit to a kinetic model that represents dynamic behavior through transfer between a series of compartments (FIG. 3). The rates $(K\_1, k\_2, k\_3, k\_4)$ at which this transfer occurs constitute the parameters of the model, see Carson, R. E. (2002), "Tracer kinetic modeling in PET", Positron Emission Tomography, Basic Science and Clinical Practice, pp. 127-159.

The kinetic models may be fit to a sequence of previously reconstructed images with one set of parameters computed from image values averaged over a user-selected region of interest in the image. These models may represent tracer uptake in terms of quantitative rate parameters and have the potential for improved clinical value over static PET but represent an average over a relatively large volume of tissue.

An alternative approach is to produce an image of one or more rate parameters by fitting the PET data to the kinetic model at each voxel in the image. See Snyder D. L. (1984), "Parameter Estimation for Dynamic Studies in Emission-Tomography Systems Having List-Mode Data", IEEE Transactions on Nuclear Science, vol. 31(2): pp. 925-931. Several computational methods have been described for this purpose See Kamasak, M. E., Bouman, C. A., Morris, E. D., Sauer, K. (2005), "Direct reconstruction of kinetic parameter images from dynamic PET data", IEEE Transactions on Medical Imaging, 2005. vol. 24(5): pp. 636-650 and Wang, G., Qi, J. (2009), "Generalized Algorithms for Direct Reconstruction of Parametric Images From Dynamic PET Data", IEEE Transactions on Medical Imaging, pp. 1717-1726.

These methods for computing parametric images from dynamic PET data may assume that continuous data is acquired from the time that the PET tracer is administered to the patient. This would therefore precludes parametric imaging of regions of the patient's body that are longer than the axial extent 202 of the scanner since the data can only be acquired for one position of the patient in the scanner.

Alternative simplified linear graphical models have been developed to compute approximate dynamic solutions. These include the Patlak model, which is a simplified kinetic model for irreversibly bound tracers that is linear with respect to its parameters, see Patlak, C. S., Blasberg, R. G., and Fenstermacher, J. D. (1983), "Graphical evaluation of blood-to-brain transfer constants from multiple-time uptake data"; Journal of Cerebral Blood Flow and Metabolism, vol.

2(1): pp. 1-7), and the Logan plot, for reversible tracers, see J. Logan, J. S. Fowler, N. D. Volkow, A. P. Wolf, S. L. Dewey, D. J. Schlyer, R. R. MacGregor, R. Hitzemann, B. Bendriem, S. J. Gatley, D. R. Christman (1990), "Graphical analysis of reversible radiolig and binding from time-activity measurements applied to [N-11C-methyl]-(−)-cocaine PET studies in human subjects," Journal of Cerebral Blood Flow and Metabolism 10 (5): 740-747.

A method for voxel-wise reconstruction of images of Patlak parameters is described by Wang et al. see Wang G., Fu, L., Qi, J. (2008), "Maximum a posteriori reconstruction of Patlak parametric image from sinograms in dynamic PET", Physics in Medicine and Biology, vol. 53: pp. 593-604). This method uses a preconditioned conjugate gradient method applied to sinogram data from a sequence of frames in a single bed position.

An alternative method fits a whole body Patlak model to previously reconstructed images at each bed position. See Karakatsanis N. A., Lodge M. A., Tahari A. K., Zhou Y., Wahl R. L., R. A. (2013), "Dynamic whole-body PET parametric imaging: I. Concept, acquisition protocol optimization and clinical application", Physics in Medicine and Biology, vol. 58(29): pp. 7391-7418. This method uses multiple passes of the patient and bed through the scanner using multiple bed positions to cover an axial extent that exceeds that of the scanner. The method does not compute the Patlak images directly from the list-mode or sinogram data but first reconstructs images from each pass using the OSEM (ordered subsets expectation maximization) algorithm and then fits the Patlak model at each voxel to these images to form a quantitative image of the Patlak slope and intercept.

These approaches do not describe methods for quantitative Patlak image reconstruction directly from multiple bed-position PET data for use in cases where the extent of the subject to be imaged exceeds the axial length of the scanner. While they analyze changes in radiotracer uptake over time using two or more passes through a scanner, each pass consisting of multiple bed positions, this analysis is applied to images that have already been separately reconstructed from the data from each pass. There may be advantages in terms of image resolution, noise properties and diagnostic power, to directly reconstructing quantitative multiple bed-position Patlak images directly from list-mode or sinogram data from two or more passes.

SUMMARY

A medical imaging system for reconstructing quantitative dynamic nuclear medicine images of a subject may include a three dimensional positron emission tomography (3D PET) scanner and a data processing system. The three dimensional positron emission tomography (3D PET) scanner may: perform scans of the subject at each of multiple bed positions, each scan being of only a sub-portion of the subject that is within an axial length covered by the scanner; and generate dynamic list-mode PET data that: represents a total number of photon pairs arriving at each of multiple detector pairs in the 3D PET scanner; and is organized in a list of elements, each element in the list including a detector pair index and an arrival time for each detected photon pair; and acquires PET data using a dynamic PET protocol with at least two scans at each of the multiple bed positions. The data processing system may: reconstruct Patlak slope and intercept images of the subject over an axial length of the subject that exceeds the axial length of each scan of the subject by optimizing a penalized likelihood function using the list-mode PET data from at least two scans of the subject at each of the multiple bed positions; and store the reconstructed image in a storage device or displays the reconstructed image on a display system.

The data processing system may compute a blood input function for the Patlak model using a an exponential model that combines prior knowledge of a population-based blood input function with estimated patient arterial blood activity levels computed from the list-mode PET data.

The data processing system may apply a resolution uniformity control scheme to achieve approximately count-independent resolution in the reconstructed Patlak images.

The data processing system may use a 4D incremental gradient method during the reconstruction of the Patlak images.

The data processing system may use an image registration method to realign the subject to the Patlak images to compensate for effects of patient motion between frames.

The dynamic protocol may perform sequential scanning at multiple bed positions that cover the axial length of the subject which may or may not be the full length of the subject such that each bed position is scanned only twice.

The dynamic protocol may include continuous bed motion that causes the axial length of the subject to pass through the scanner twice.

The data processing system may convert the list-mode PET data into a sinogram format before optimizing the penalized likelihood function.

The penalized likelihood function may include a penalty term that is set to zero, resulting in optimization of a likelihood function.

A non-transitory, tangible, computer-readable storage media may contain a program of instructions that may cause a three dimensional positron emission tomography (3D PET) scanner and a data processing system running the program of instructions to perform any one or more of the functions that are recited herein for these components.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
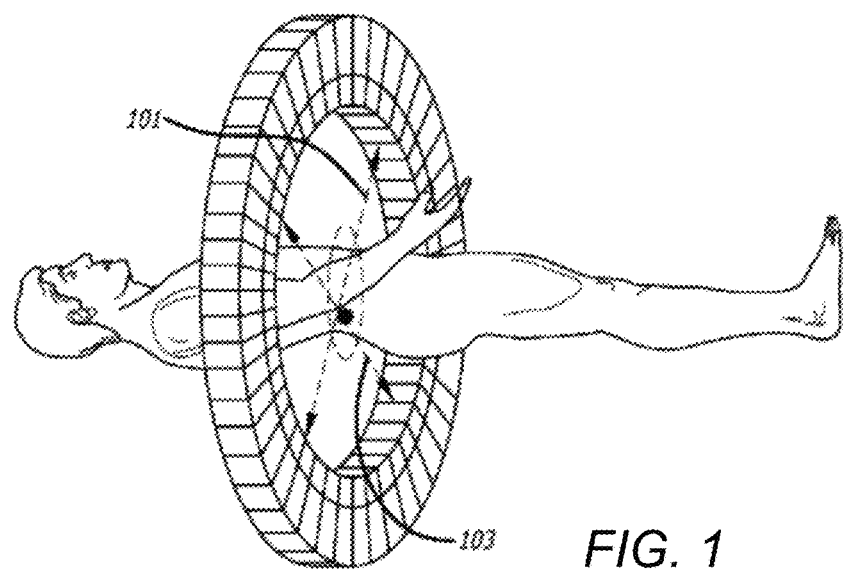
FIG. 1 illustrates an example of a ring of detectors in a single-ring PET scanner.

FIG. 1 illustrates an example of a ring of detectors in a single-ring PET scanner.

Figure 2:
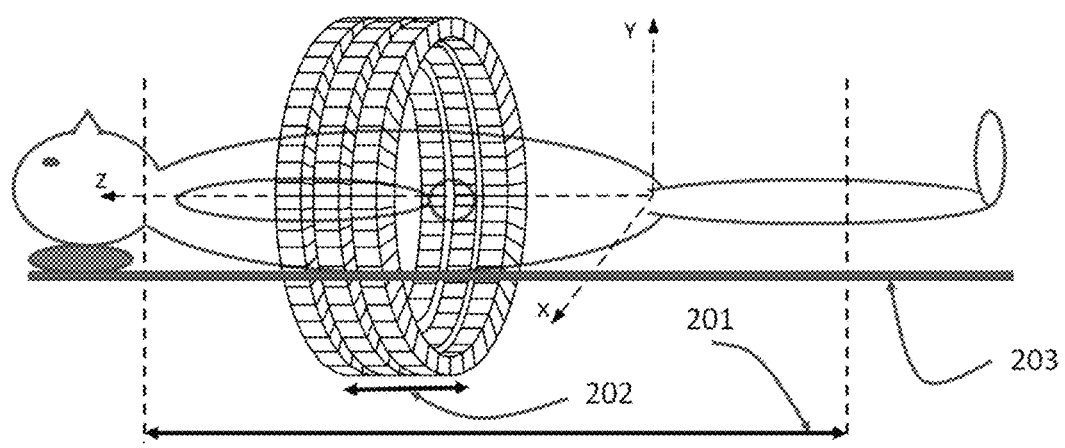
FIG. 2 illustrates an example of a three dimensional (3D)PET scanner.
Figure 3:
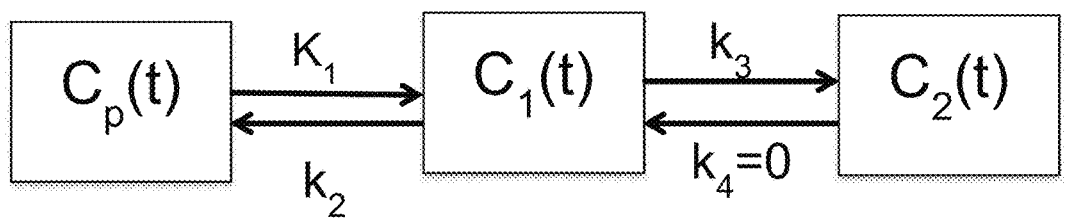
FIG. 3 illustrates an example of a two-compartment kinetic model that may be used for dynamic PET imaging.

FIG. 2 illustrates am example of a three dimensional (3D)PET scanner.

Approaches for the reconstruction of parametric whole or extended body PET images are now described, whose axial length 201 exceeds an axial extent 202 of a scanner, from list-mode PET data using a Patlak model to represent tracer dynamics.

Figure 4:
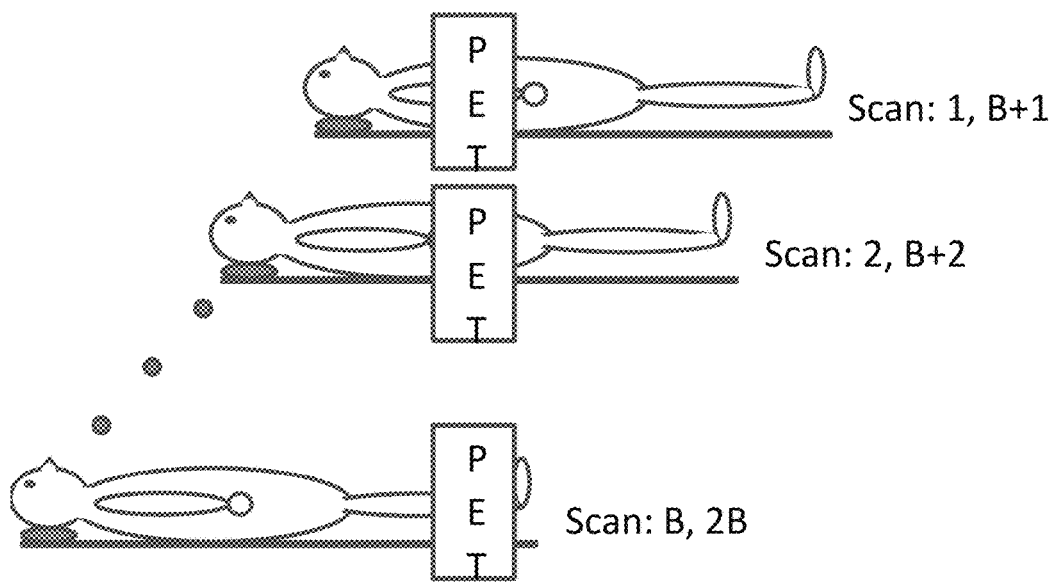
FIG. 4 illustrates an example of dynamic PET scanning at multiple bed positions during which each bed position is scanned twice.

FIG. 4 illustrates an example of dynamic PET scanning at multiple bed positions during which each bed position is scanned twice.

By stepping or moving the patient through the scanner two or more times, as shown in FIG. 4, a set of scans, each including a set of list-mode data acquired with the patient in a particular location in the scanner, may be acquired. The Patlak slope and intercept images may be reconstructed by combining the data from these scans using an image reconstruction data processing system that may include software. A penalized maximum likelihood numerical optimization method may be used to reconstruct the images by combining the data from two of more scans per bed position with a model of the PET system, a model for the statistical distribution of noise in the data, and a numerical penalty function. The penalty function may be used to control the resolution and noise properties of the reconstructed Patlak images.

To account for patient motion during scanning, the reconstruction method may include a registration step between the two frames at each position in the scanner. The blood input function required for the Patlak model may be estimated from the image data in combination with a population based average input function. The method is capable of performing robust estimation of Patlak images from as few as two acquisition frames per bed position. This method may therefore be used for dynamic whole body imaging or other protocols that require images of the subject over an axial extent that exceeds that of the scanner.

The penalized maximum likelihood cost function that is numerically optimized may allow reconstruction of images whose resolution is independent of tracer activity and matched between the slope and intercept Patlak parameters. Overall image resolution may be controlled by the user varying a single parameter.

To produce images of the Patlak parameters over portions of the subject body that exceed the length of the scanner, list-mode data may be acquired by scanning multiple sub-portions of the body, each of which fits within the axial extent of the scanner. The patient may be moved through in discrete steps as illustrated in FIG. 4 with list-mode data acquired for a period of typically 1-5 minutes at each step. After all desired sub-portions have been scanned, the process may be repeated at least once more so that a minimum of two scans are acquired over each sub portion.

A delay between the sets of scans may be included in the imaging protocol to allow, for example, for an x-ray CT transmission scan when used in a combined PET/CT scanner. The duration of each scan need not be the same and the order in which they are acquired may be varied from one pass to the next. List-mode data for Patlak imaging may also be acquired using continuous bed motion by performing a minimum of two passes of the patient through the scanner.

The Patlak model may provide an approximate solution to the two compartment kinetic model for irreversible tracers in the steady state period $t \geq T_0$ in which changes may be effectively due to irreversible trapping in a single compartment. Let $\eta(t)$ be the tracer time activity curve (TAC) with blood input function C(t). The Patlak equation may be written as:

$$\eta(t) = \kappa \int_0^t C(\tau) d\tau + qC(t) \quad (1)$$

where $\kappa$ is the net influx rate or slope parameter, and q is the intercept of the Patlak model.

The rate function at voxel j after steady state $t \geq T_0$ therefore may be represented as a linear combination of two basis functions $B_1(t)$ and $B_2(t)$:

$$\eta_j(t) = \sum_{l=1}^{2} w_{jl} B_l(t) \quad (2)$$

Here, $w_{j1} = \kappa_j, w_{j2} = q_j, B_1(t) = \int_0^t C(\tau)d\tau, B_2(t) = C(t)$. The rate function representing the time varying rate of coincidence detection at line of response (LOR) i may be written as:

$$\lambda_i(t) = e^{-t/\tau} \sum_{j=1}^{n_v} \sum_{l=1}^{2} p_{ij} w_{jl} B_l(t) + r_i(t) + s_i(t) \quad (3)$$

where the exponential term accounts for radioactive decay of the tracer with half-life $\tau \text{Log}(2)$; $p_{ij}$ is the probability of an event at voxel j being detected at detector pair i; and $n_v$ is the number of voxels. The additional terms $r_i(t)$ and $s_i(t)$ denote, respectively, randoms and scattered coincidence rate functions. A factored system model for $p_{ij}$ based on a product of attenuation factors, normalization, geometric response, and a Monte Carlo model of the detector response may be used See Qi, J., Leahy, R. M., Cherry, S. R., Chatziioannou, A., Farquhar, T. H. (1998), "High Resolution 3D Bayesian Image Reconstruction Using the MicroPET Small-animal Scanner", Physics in Medicine and Biology, vol. 43(4): pp. 1001-1013. The random and scatter rate functions may be estimated prior to image reconstruction. They may be assumed to be separable into spatial and temporal factors as described below.

With continuously collected list-mode data over time interval $[T_0, T]$ and the arrival times in the list-mode data following an inhomogeneous Poisson model, the log-likelihood function of event arrival times may be given by:

$$L(W) = -\sum_{i=1}^{n_p} \sum_{k=1}^{x_i} \log \lambda_i(a_{ik}) + \sum_{i=1}^{n_p} \int_{T_0}^{T} \lambda_i(t) dt \quad (4)$$

where $a_{ik}$ denotes the arrival time of the k'th photon at detector pair i, $x_i$ is the number of events detected in LOR i and $n_p$ is the total number of LORs. In the case where two frames of data are collected over two subintervals $[T_1 \ T_2]$ and $[T_3 \ T_4]$, then $$L(W) = -\sum_{i=1}^{n_p} \sum_{k=1}^{x_i} \log \lambda_i(a_{ik}) + \sum_{i=1}^{n_p} \left( \int_{T_1}^{T_2} \lambda_i(t) dt + \int_{T_3}^{T_4} \lambda_i(t) dt \right) \quad (5)$$

where the $a_{ik}$ are constrained to those events detected in the intervals $[T_1 \ T_2]$ and $[T_3 \ T_4]$. For whole-body imaging, there may be multiple bed positions (b=1, ... B) (FIG. 4), each with distinct data acquisition intervals $[T_1^b T_2^b]$ and $[T_3^b, T_4^b]$, so that whole body reconstruction (5) may also include a sum over bed position index b in the last term:

$$L(W) = -\sum_{i=1}^{n_p}\sum_{k=1}^{x_i} \log\lambda_i(a_{ik}) + \sum_{b=1}^{B}\sum_{i=1}^{n_p}\left(\int_{T_1^b}^{T_2^b}\lambda_i(t)dt + \int_{T_3^b}^{T_4^b}\lambda_i(t)dt\right) \quad (6)$$

If more than two frames are collected at any bed position, then (6) may be modified to include summations over each additional frame at each bed position. To avoid unnecessary notational complexity, these summations in the sequel may be omitted, but all of the following equations may also be modified to include multiple frames per bed position.

The log-likelihood function may be regularized with a quadratic spatial penalty function to compute images of the Patlak slope and intercept:

$$F(W) = -\Sigma_{i=1}^{n_p}\Sigma_{k=1}^{x_i}\log\lambda_i(a_{ik}) + \Sigma_{b=1}^{B}\Sigma_{i=1}^{n_p}(\int_{T_1^b}^{T_2^b}\lambda_i(t)dt + \int_{T_3^b}^{T_4^b}\lambda_i(t)dt) + \beta \tfrac{1}{2}w^T R_S w \quad (7)$$

where $w = w_{jl}$ is a $2n_v$ length vector containing the Patlak slope and intercept image values for each voxel, $w_{jl}$ is indexed by voxel index $j=1, \ldots n_v$, and basis $l=1,2$ (for slope and intercept respectively). $R_S$ is a $2n_v \times 2n_v$ matrix that may compute the weighted squared pairwise difference between each voxel and its spatial nearest neighbors separately for both slope and intercept images.

The list-mode data for each scan may also first be sorted into sets of sinogram data $\{S_i^{12b}, i=1, \ldots n_p, b=1, \ldots B\}$ and $\{S_i^{34b}, i=1, \ldots n_p, b=1, \ldots B\}$, for the first and second pass, respectively. For sorting of PET data into sinogram format, see B Bendriem and DW Townsend (eds), "The Theory and Practice of PET", Kluwer Academic Press, 1998. The Patlak slope and intercept images may then be reconstructed jointly from the two pass sinogram, using the modified penalized likelihood function:

$$F(W) = -\Sigma_{b=1}^{B}\Sigma_{i=1}^{n_p}\{S_i^{12b}\log\int_{T_1^b}^{T_2^b}\lambda_i(t)dt + S_i^{34b}\log\int_{T_3^b}^{T_4^b}\lambda_i(t)dt\} + \Sigma_{b=1}^{B}\Sigma_{i=1}^{n_p}(\int_{T_1^b}^{T_2^b}\lambda_i(t)dt + \int_{T_3^b}^{T_4^b}\lambda_i(t)dt) + \beta\tfrac{1}{2}w^T R_S w \quad (8)$$

Sinogram data may be pre-corrected for randoms and/or scatter in which case the penalized likelihood in (8) may be modified to account for these changes. See Q. Li and R M Leahy, Statistical modeling and reconstruction of randoms pre-corrected PET data, IEEE Trans. Med. Imag, 25(12): 1565-1572, 2006.

Continuous bed motion may be used. In this case, the data may first be transformed into a patient-centered coordinate system that accounts for the relative motion of patient and scanner during data acquisition. This may require reassignment of LOR indices for each list mode event into LORs that are fixed with respect to the patient coordinate system. See U.S. Pat. No. 6,915,004 B2, Newport D F, Casey M E, Luk W K, Reed J H (2002). After this transformation, the Patlak images may be computed by application of the penalized likelihood (eq. 7), or if data are first sorted into sinograms, the alternative penalized likelihood (eq. 8).

The spatial penalty can have various forms which may include:

$$\tfrac{1}{2}w^T R_S w = \Sigma_{l=1}^{2}\Sigma_{j=1}^{n_v}\Sigma_{j' \in N_{j,j'>j}}\mu_{jl,j'l'}(w_{jl}-w_{j'l})^2 \quad (9)$$

where the weights $\mu_{jl,j'l'}$ can either (i) define a shift invariant penalty by setting them equal to the inverse of the Euclidean distance between the two voxels, or (ii) be precomputed from the data to ensure count independent resolution in the Patlak slope and intercept images. In (9), $N_j$ represents a neighborhood of voxels surrounding voxel j, which may include the 26 neighbors forming a 3-voxel sided cube surrounding voxel j or some symmetric subset of these.

A 4D incremental gradient (4DIG) method may be used to optimize (6) see Q. Li, E. Asma, S. Ahn, and R. M. Leahy, "A Fast Fully 4D Incremental Gradient Reconstruction Algorithm for List Mode PET Data". IEEE Trans. Med. Imag, 2007. 26(1): p. 58-67. 4DIG iterates over subsets of data in such a way as to ensure convergence to a maximum of F(W) in (7). The updated equation for this algorithm may have the form:

$$w^{n,m} = P_\tau[w^{n,m-1} + \alpha_n D(w^{n,m-1})\nabla f_m(w^{n,m-1})] \quad (10)$$

where n denotes the iteration number, m denotes the sub-iteration number, $f_m$ denotes the $m^{th}$ sub-objective function, $D(w^{n,m-1})$ is a diagonal preconditioning matrix, and $P_\tau$ is a projection operator used to ensure convergence to a local maximum. Unlike the full parametric model, the Patlak formulation may result in a concave cost function so that any local maximum is a global maximum. Other numerical optimization algorithms may also be used to maximize (7), including conjugate gradient, other forms of incremental gradient method, ordered subsets, iterated and grouped coordinate ascent, and augmented Lagrangian methods. These methods may also be used to optimize the modified penalized likelihood function (8) when the data are first sorted into sinograms. Setting the parameter $\beta$ to zero in (7) or (8) reduces the approach to maximum likelihood which may also be used to compute the Patlak slope and intercept images.

Iterative image reconstruction methods that use the Poisson likelihood function in (6) or (7) may produce images whose resolution varies spatially with the amount of tracer. This may be the case for static as well as dynamic image reconstruction, whether using list-mode or sinogram data. The system may reconstruct images with count independent resolution by appropriate selection of the weights $\mu_{jl,j'l'}$ in (8).

To control image resolution in the reconstructed Patlak images, the local impulse response (LIR) at voxel j may be used, which may correspond to the mean change in the reconstructed image in response to a perturbation of the true source distribution at that pixel. In the case of linear estimators, this may correspond to the standard source-independent impulse response of the system. However, for nonlinear estimators, the LIR may be dependent on the underlying source distribution. The LIR at voxel j may be approximated as:

$$LIR^j(\tilde{w}) = [F + \beta R_s]^{-1} F e^j \quad (11)$$

where $\tilde{w}$ is the estimated Patlak image, F is the Fisher Information Matrix (FIM), $e^j$ is the unit vector at voxel $j \in \{1,2, \ldots, 2n_v\}$, and $R_s$ is the quadratic penalty function with $\beta$ a global (scalar) smoothing parameter.

In (11), the FIM is a function of the spatial distribution of the radiotracer in the subject and, as a result, the LIR may vary across the image depending on the FIM. To remove this dependence, the matrix $R_S$ from the penalty function in (7) may be modified so that the right hand side of (11), and therefore the resolution properties, become approximately independent of the tracer distribution. This may be achieved by appropriate choice of the parameters in the right hand side of (9) that define matrix $R_S$.

A derivation of these parameters is included in Zhu, W., Li, Q., Bai, B., Conti, P., & Leahy (2014), R., Patlak Image Estimation From Dual Time-Point List-Mode PET Data. IEEE Transactions on Medical Imaging, Vol. 33(4), pp. 913-924. Approximately count independent resolution may result from the following definition of the parameters in (9):

$$\mu_{jl,j'l'} = 1/\theta_{jl}\theta_{j'l'}E_{jj'} \quad (12)$$

for j'∈$N_j$, where $E_{jj'}$ is the Euclidean distance between the two voxels and $$\theta_{jl} = \sqrt{\frac{\sum_{i=1}^{n_d} p_{ij}^2 \left( \int_{T_1}^{T_2} \frac{\tilde{B}_l^2(t)}{\lambda_i(t)} dt + \int_{T_3}^{T_4} \frac{\tilde{B}_l^2(t)}{\lambda_i(t)} dt \right)}{\sum_{i=1}^{n_d} p_{ij}^2 \left( \int_{T_1}^{T_2} \tilde{B}_l^2(t) dt + \int_{T_3}^{T_4} \tilde{B}_l^2(t) dt \right)}} \quad (13)$$

To ensure that the resolution of the Patlak slope image is matched to that of the Patlak intercept image, the temporal basis function $B_2(t)$ may also be scaled by the factor:

$$\alpha = \sqrt{\frac{\left(\int_{T_1}^{T_2} \tilde{B}_1(t) dt\right)^2 + \left(\int_{T_3}^{T_4} \tilde{B}_1(t) dt\right)^2}{\left(\int_{T_1}^{T_2} \tilde{B}_2(t) dt\right)^2 + \left(\int_{T_3}^{T_4} \tilde{B}_2(t) dt\right)^2}} \quad (14)$$

These expressions are for two frames in a single bed position. For the penalized likelihood function in (7) for the multiple bed position case, the parameters are:

$$\theta_{jl} = \sqrt{\frac{\sum_{b=1}^{B} \sum_{i=1}^{n_d} p_{ij}^2 \left( \int_{T_1^b}^{T_2^b} \frac{\tilde{B}_l^2(t)}{\lambda_i(t)} dt + \int_{T_3^b}^{T_4^b} \frac{\tilde{B}_l^2(t)}{\lambda_i(t)} dt \right)}{\sum_{b=1}^{B} \sum_{i=1}^{n_d} p_{ij}^2 \left( \int_{T_1^b}^{T_2^b} \tilde{B}_l^2(t) dt + \int_{T_3^b}^{T_4^b} \tilde{B}_l^2(t) dt \right)}} \quad (15)$$

and scaling of the temporal basis for the bth bed position is:

$$\alpha_b = \sqrt{\frac{\left(\int_{T_1^b}^{T_2^b} \tilde{B}_1(t) dt\right)^2 + \left(\int_{T_3^b}^{T_4^b} \tilde{B}_1(t) dt\right)^2}{\left(\int_{T_1^b}^{T_2^b} \tilde{B}_2(t) dt\right)^2 + \left(\int_{T_3^b}^{T_4^b} \tilde{B}_2(t) dt\right)^2}} \quad (16)$$

Routine measurement of the blood input function C(t) using arterial sampling may be impractical in clinical practice. The system may use a hybrid approach that combines a population based estimate for the early scan time (t<$t_1$) with an image-based exponential model for the rest of the scan time (t>$t_1$), where $t_1$ is a user selected constant on the order of the time to steady state of the Patlak model.

A population based input function may be estimated from the input function for a group of subjects based on arterial samples or dynamic PET studies in which large arterial vessels are scanned throughout the early scan time. Each input function may be first scaled to have unit integral under the curve and the resulting curves averaged to form $C_{standard}$(t).

For the hybrid estimation method, two additional blood pool measurements may be made from two frames of the subject PET data for a bed position in which a large arterial vessel, such as the abdominal aorta, is visible. The constants μ, β, γ that define the input function for the subject may be determined from these two additional samples and $C_{standard}$(t) so that the input function is continuous at $t_1$:

$$C(t) = \begin{cases} \mu C_{standard}(t) & t < t_1 \\ \beta \exp(\gamma t) & t > t_1 \end{cases} \quad (17)$$

A continuous-time estimate of the randoms and scatter contributions to the data may be needed for direct dynamic image reconstruction. The whole-body protocol may be composed of 2 list mode acquisition frames for each of several bed positions. The temporal and spatial distribution of scatters and randoms may be assumed to be separable for each frame. Randoms rate functions may be estimated as the product of the random sinogram averaged over the entire frame duration and a temporal variation function reflecting the dynamic change in overall randoms rate over the duration of the frame. Similarly, the scatter rate function may be modeled as the product of the scatter sinogram for the frame and a dynamic change in overall scatter rate over the duration of the frame.

The randoms sinogram may be computed from a sinogram of delayed events summed over the acquisition period or from the singles rates. The scatter sinogram may be computed using a standard static scatter modeling method based on the sinogram for the frame and a co-registered x-ray CT scan. The temporal rate function of scatters for each bed position may be assumed to be proportional to the rate function of prompts, and then normalized to unity over the frame. A similar process may be used for estimating the randoms rate function, but varying in proportion to the square of activity.

Patients may move during the scan. Reconstructed static PET images from each acquisition frame may be used to ensure alignment of the patient between frames. In the event that the patient has moved, a non-rigid image registration method may be used to determine an image deformation map that will allow deformation of the estimated PET image between frames to ensure that the patient alignment is consistent with the data model throughout the scanning period. See J B Maintz and M A Viergever (1998) A survey of medical image registration, Med. Imag. Anal. 2: 1-36 and W. Zhu, B. Bai, P. S. Conti, Q. Li, and R. M. Leahy (2013), Data Correction Methods for Wholebody Patlak Imaging from List-mode PET Data, Meeting on Fully 3D Image Reconstruction in Radiology and Nuclear Medicine, Lake Tahoe, Calif., pp. 213-216.

Figure 5:
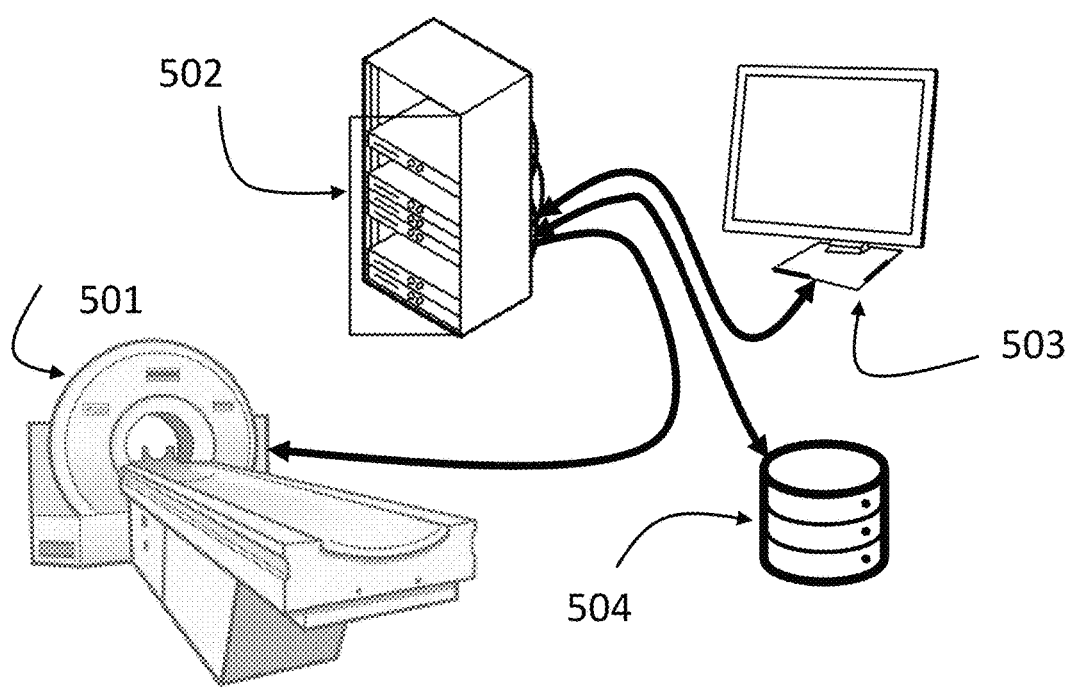
FIG. 5 illustrates an example of a medical imaging system that reconstructs, stores and displays Patlak slope and intercept images.

FIG. 5 illustrates an example of a medical imaging system that reconstructs, stores and displays Patlak slope and intercept images. As illustrated in FIG. 5, the system may include a scanner 501 having a patient bed that moves horizontally in any of the ways described herein and that scans a portion of a patient in any of the ways described herein, a data processing system 502 that may perform one or more of the data processing functions described herein, a display 503 that may display any of the images described herein, and a data storage system 504 that may store any of the types of information, images and/or data that have been described herein.

The data processing system 502 may be implemented with a computer system configured to perform the functions that have been described herein for the component. The computer system may include one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

For example, any dynamic whole or partial body scanning protocol may be used that acquires list mode data over an extent that exceeds the axial length of the scanner using either step-and-shoot or continuous bed motion. Reconstruction using penalized likelihood may be used where the likelihood function represents the Poisson distribution or variations on the distribution of list-mode or sinogram-sorted data to account for the effects of data preprocessing. Systems may be used in which sinogram sorting of the list-mode data is performed in hardware before transfer of the data to the system computer. Any numerical optimization method other than 4DIG may be used to find an image that approximately maximizes a penalized likelihood function. Non-quadratic penalty functions may be used that preserve edges in the reconstructed image. Systems may be used that include data processing in which the penalty term in (7) or (8) is set to zero.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A medical imaging system for reconstructing quantitative dynamic nuclear medicine images of a subject comprising:
   a three dimensional positron emission tomography (3D PET) scanner that:
      performs scans of the subject at each of multiple bed positions, each scan being of only a sub-portion of the subject that is within an axial length covered by the scanner;
      generates dynamic list-mode PET data that:
         represents a total number of photon pairs arriving at each of multiple detector pairs in the 3D PET scanner; and
         is organized in a list of elements, each element in the list including a detector pair index and an arrival time for each detected photon pair; and
      acquires PET data using a dynamic PET protocol with at least two scans at each of the multiple bed positions;
   a data processing system that:
      reconstructs Patlak slope and intercept images of the subject over an axial length of the subject that exceeds the axial length of each scan of the subject by optimizing a penalized likelihood function using the list-mode PET data from at least two scans of the subject at each of the multiple bed positions, the penalized likelihood function including:
- a model for the 3D PET scanner and for statistical distribution of noise in the data from multiple bed positions; and
- a numerical penalty function; and stores the reconstructed Patlak slope and intercept images in a storage device or displays the reconstructed Patlak slope and intercept images on a display system.

2. The medical imaging system of claim 1 wherein the data processing system computes a blood input function for a Patlak model using an exponential model that combines prior knowledge of a population-based blood input function with estimated patient arterial blood activity levels computed from the list-mode PET data.

3. The medical imaging system of claim 1 wherein the data processing system applies a resolution uniformity control scheme to achieve approximately count-independent resolution in the reconstructed Patlak slope and intercept images.

4. The medical imaging system of claim 1 wherein the data processing system uses a 4D incremental gradient method during the reconstruction of the Patlak slope and intercept images.

5. The medical imaging system of claim 1 wherein the data processing system uses an image registration method to realign the subject to the Patlak slope and intercept images to compensate for effects of patient motion between frames.

6. The medical imaging system of claim 1 wherein the dynamic PET protocol performs sequential scanning at multiple bed positions that cover the axial length of the subject which may or may not be the full length of the subject such that each bed position is scanned only twice.

7. The medical imaging system of claim 1 wherein the dynamic PET protocol includes continuous bed motion that causes the axial length of the subject to pass through the scanner twice.

8. The medical imaging system of claim 1 wherein the data processing system converts the list-mode PET data into a sinogram format before optimizing the penalized likelihood function.

9. The medical imaging system of claim 1 wherein the penalized likelihood function includes a penalty term that is set to zero, resulting in optimization of a likelihood function.

10. A non-transitory, tangible, computer-readable storage media containing a program of instructions that causes a three dimensional positron emission tomography (3D PET) scanner and a data processing system running the program of instructions to function as a medical imaging system for reconstructing quantitative dynamic nuclear medicine images of a subject that:
- performs scans of the subject at each of multiple bed positions, each scan being of only a sub-portion of the subject that is within an axial length covered by the scanner;
- generates dynamic list-mode PET data that:
  - represents a total number of photon pairs arriving at each of multiple detector pairs in the 3D PET scanner; and
  - is organized in a list of elements, each element in the list including a detector pair index and an arrival time for each detected photon pair; and
- acquires PET data using a dynamic PET protocol with at least two scans at each of the multiple bed positions;
- reconstructs Patlak slope and intercept images of the subject over an axial length of the subject that exceeds the axial length of each scan of the subject by optimizing a penalized likelihood function using the list-mode PET data from at least two scans of the subject at each of the multiple bed positions, the penalized likelihood function including:
  - a model for the 3D PET scanner and for statistical distribution of noise in the data from multiple bed positions; and
  - a numerical penalty function; and
- stores the reconstructed Patlak slope and intercept images in a storage device or displays the reconstructed image on a display system.

11. The storage media of claim 10 wherein the program of instructions when run computes a blood input function for a Patlak model using an exponential model that combines prior knowledge of a population-based blood input function with estimated patient arterial blood activity levels computed from the list-mode PET data.

12. The storage media of claim 10 wherein the program of instructions when run applies a resolution uniformity control scheme to achieve approximately count-independent resolution in the reconstructed Patlak slope and intercept images.

13. The storage media of claim 10 wherein the program of instructions when run uses a 4D incremental gradient method during the reconstruction of the Patlak slope and intercept images.

14. The storage media of claim 10 wherein the program of instructions when run uses an image registration method to realign the subject to the Patlak slope and intercept images to compensate for effects of patient motion between frames.

15. The storage media of claim 10 wherein the dynamic PET protocol performs sequential scanning at multiple bed positions that cover the axial length of the subject which may or may not be the full length of the subject such that each bed position is scanned only twice.

16. The storage media of claim 10 wherein the dynamic PET protocol includes continuous bed motion that causes the axial length of the subject to pass through the scanner twice.

17. The storage media of claim 10 wherein the program of instructions when run converts the list-mode PET data into a sinogram format before optimizing the penalized likelihood function.

18. The storage media of claim 10 wherein the penalized likelihood function includes a penalty term that is optimized and set to zero, resulting in optimization of a likelihood function.

* * * * *